(12) United States Patent
Okuyama et al.

(10) Patent No.: US 9,332,932 B2
(45) Date of Patent: May 10, 2016

(54) BLOOD COLLECTING PUNCTURE DEVICE AND MAGAZINE USED FOR THE SAME

(75) Inventors: Koji Okuyama, Ehime (JP); Akio Nagao, Ehime (JP); Yoshiki Takeuchi, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 720 days.

(21) Appl. No.: 12/922,616

(22) PCT Filed: Mar. 18, 2009

(86) PCT No.: PCT/JP2009/001220
§ 371 (c)(1),
(2), (4) Date: Sep. 14, 2010

(87) PCT Pub. No.: WO2009/116289
PCT Pub. Date: Sep. 24, 2009

(65) Prior Publication Data
US 2011/0022071 A1  Jan. 27, 2011

(30) Foreign Application Priority Data
Mar. 18, 2008 (JP) .................................. 2008-069043

(51) Int. Cl.
*A61M 5/32* (2006.01)
*A61B 5/15* (2006.01)
*A61B 5/151* (2006.01)

(52) U.S. Cl.
CPC ......... *A61B 5/1411* (2013.01); *A61B 5/150022* (2013.01); *A61B 5/15113* (2013.01);
(Continued)

(58) Field of Classification Search
CPC ........... A61B 5/1411; A61B 5/150022; A61B 5/15146; A61B 5/15153; A61B 5/15178

USPC ................................................... 606/181, 182
See application file for complete search history.

(56) References Cited

U.S. PATENT DOCUMENTS 5,951,582 A * 9/1999 Thorne et al. .................. 606/182
7,211,096 B2 * 5/2007 Kuhr et al ...................... 606/182
(Continued)

FOREIGN PATENT DOCUMENTS

JP   2002-143132   5/2002
JP   2004-512129   4/2004
(Continued)

OTHER PUBLICATIONS

Search report from E.P.O., mail date is May 14, 2013.

*Primary Examiner* — Julie A Szpira
(74) *Attorney, Agent, or Firm* — Greenblum & Bernstein, P.L.C.

(57) ABSTRACT

Provided are a blood collecting puncture device having high safety which can hygienically maintain the inside of a magazine and prevent infection, and the magazine. A blood collecting puncture device has a blood collecting puncture device body removably incorporating a magazine for housing lancets for puncturing human skin. The blood collecting puncture device body has a first housing section for housing not-yet-used lancets and a second housing section for housing used lancets to be disposed of. When a rotor is rotated, individual lancets are sequentially conveyed on a one-by-one basis to a stock position, a puncture position, and a disposal position, and this causes a not-yet-used lancet to be housed in the first housing section and also causes a used lancet to be housed in the second housing section, so that the lancets are separately housed in spaces isolated from each other.

15 Claims, 11 Drawing Sheets

(52) U.S. Cl.
CPC ......... *A61B5/15117* (2013.01); *A61B 5/15146* (2013.01); *A61B 5/15153* (2013.01); *A61B 5/15174* (2013.01); *A61B 5/15178* (2013.01); *A61B 5/15186* (2013.01); *A61B 5/150435* (2013.01); *A61B 5/150519* (2013.01); *A61B 5/150564* (2013.01); *A61B 5/150725* (2013.01); *A61B 5/15019* (2013.01); *A61B 5/15176* (2013.01)

(56) References Cited

U.S. PATENT DOCUMENTS

| | | | |
|---|---|---|---|
| 7,731,729 B2 * | 6/2010 | Freeman et al. | 606/181 |
| 8,029,525 B2 * | 10/2011 | Iio et al. | 606/182 |
| 2002/0120216 A1 * | 8/2002 | Fritz et al. | 600/583 |
| 2003/0211619 A1 * | 11/2003 | Olson et al. | 436/44 |
| 2004/0034318 A1 | 2/2004 | Fritz et al. | |
| 2004/0230216 A1 | 11/2004 | Levaughn et al. | |
| 2005/0027211 A1 | 2/2005 | Kuhr et al. | |
| 2005/0232815 A1 | 10/2005 | Ruhl et al. | |
| 2005/0245845 A1 | 11/2005 | Roe et al. | |
| 2005/0245954 A1 | 11/2005 | Roe et al. | |
| 2006/0099108 A1 | 5/2006 | List et al. | |
| 2006/0229652 A1 * | 10/2006 | Iio et al. | 606/182 |
| 2006/0264996 A1 * | 11/2006 | LeVaughn et al. | 606/181 |
| 2007/0173740 A1 | 7/2007 | Chan et al. | |
| 2007/0173741 A1 | 7/2007 | Deshmukh et al. | |
| 2008/0021492 A1 | 1/2008 | Freeman et al. | |
| 2008/0300509 A1 | 12/2008 | Hoenes et al. | |
| 2009/0137931 A1 | 5/2009 | Chan et al. | |
| 2010/0130997 A1 * | 5/2010 | LeVaughn et al. | 606/172 |
| 2010/0160941 A1 * | 6/2010 | Konya et al. | 606/182 |
| 2011/0160759 A1 * | 6/2011 | Schraga et al. | 606/172 |

FOREIGN PATENT DOCUMENTS

| | | |
|---|---|---|
| JP | 2006-504506 | 2/2006 |
| JP | 2006-511264 | 4/2006 |
| JP | 2007535351 | 6/2007 |
| JP | 2007535388 | 6/2007 |
| JP | 2007-535351 | 12/2007 |
| JP | 2007-535388 | 12/2007 |
| JP | 2008-296015 | 12/2008 |
| WO | 2004/041082 | 5/2004 |
| WO | 2004/060174 | 7/2004 |
| WO | 2007/077212 | 7/2007 |

* cited by examiner

BLOOD COLLECTING PUNCTURE DEVICE AND MAGAZINE USED FOR THE SAME

TECHNICAL FIELD

The present invention relates to a blood sampling puncturing device and a magazine to puncture skin and sample blood when a blood sugar level measurement and so forth are performed using a simple blood sugar measuring apparatus.

BACKGROUND ART

Conventionally, various puncturing devices for sampling blood and disposable lancets to use with these puncturing devices have been developed. A puncturing device using a lancet once and discarding it per puncturing operation has problems as follows. When a lancet is mounted in and removed from a puncturing device, a hand and so forth are punctured erroneously with a puncture needle exposing from one end of the lancet. In addition, it is troublesome to mount/remove lancets.

Patent Document 1 discloses a magazine type puncturing device in which a plurality of lancets are stored.

FIG. 1 is an exploded perspective view of a magazine type blood sampling puncturing device described in Patent Document 1.

As shown in FIG. 1, magazine type puncturing device 10 includes a plurality of puncturing members 18. The plurality of puncturing members 18 are radially arranged along groove 24 formed on the circumference of circular cartridge 12. After being set in blood sampling device 10, circular cartridge 12 rotates in the circumferential direction by pressing a charging button (not shown), so that new puncturing member 18 is held by linear actuator 56 provided with puncturing member moving and assembling member 34 and charged.

Afterward, puncturing member 18 extends by pressing a puncturing button (not shown) and punctures tissue such as skin. After puncturing, puncturing member 18 immediately parts from skin and returns into the circular cartridge. In addition, blood exuding from skin is measured and analyzed in a separate blood analysis apparatus.

When puncturing is newly performed the next time, circular cartridge 12 is rotated in the circumferential direction by operating again the charging button, so that it is possible to set new puncturing member 18.

As for this magazine type puncturing device, it is possible to replace a magazine in whole, including lancets stored inside, so that the lancets are not directly touched, and therefore, safe operations, including mounting, puncturing and discarding, are allowed.

Patent Document 1: Published Japanese Translation of PCT Application 2006-504506

DISCLOSURE OF INVENTION

Problems to be Solved by the Invention

The user does not have to directly handle lancets one-by-one by using the above-described magazine type puncturing device, so that safety is assured to prevent needle stick injury.

However, with conventional magazine puncturing devices, lancets before use and lancets after use resides in the same space in a magazine, that is, lancets stained with blood after use are not separated from lancets before use. Therefore, the problem of sanitation in a magazine remains, and it is necessary to further improve safety against infection and so forth.

It is therefore an object of the present invention to provide a blood sampling puncturing device and a magazine allowing improvement of sanitation in a magazine and the safety by prevention of infection.

Solution to Problem

The blood sampling puncturing device according to the present invention adopts a configuration in which, in the blood sampling puncturing device that removably incorporates a magazine in which a plurality of lancets each having a needle to puncture skin are stored, the magazine separately stores lancets before use and lancets after use in spaces isolated from one another.

The magazine according to the present invention adopts a configuration in which the magazine mounted in a blood sampling puncturing device that punctures skin using a needle stores a plurality of lancets each having the needle, and separately stores lancets before use and lancets after use in spaces apart from one another.

Advantageous Effects of Invention

According to the present invention, it is possible to store lancets before use and lancets after use in separate and isolated spaces, and therefore, it is possible to improve sanitation and safety by prevention of infection.

BEST MODE FOR CARRYING OUT THE INVENTION

Now, embodiments of the present invention will be described in detail with reference to the accompanying drawings.

Embodiment 1

Figure 1:
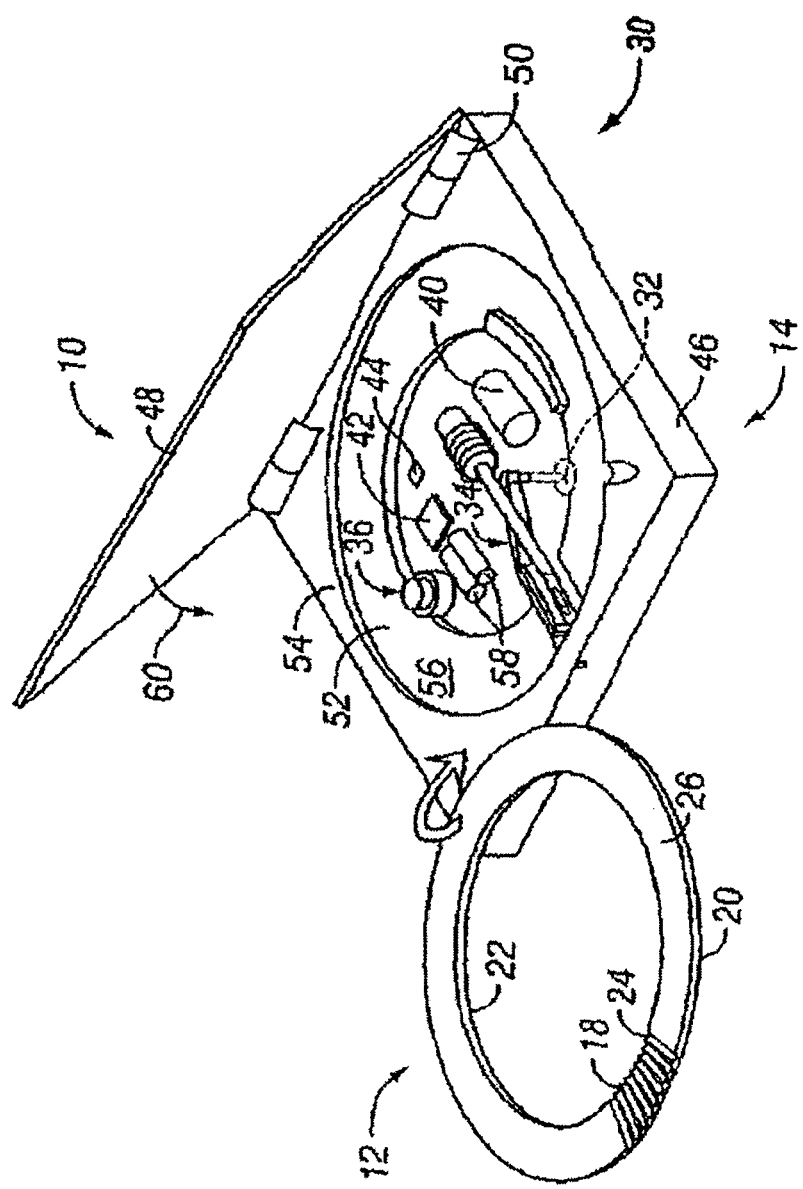
FIG. 1 is an exploded perspective view of a conventional magazine type blood sampling puncturing device.
Figure 2:
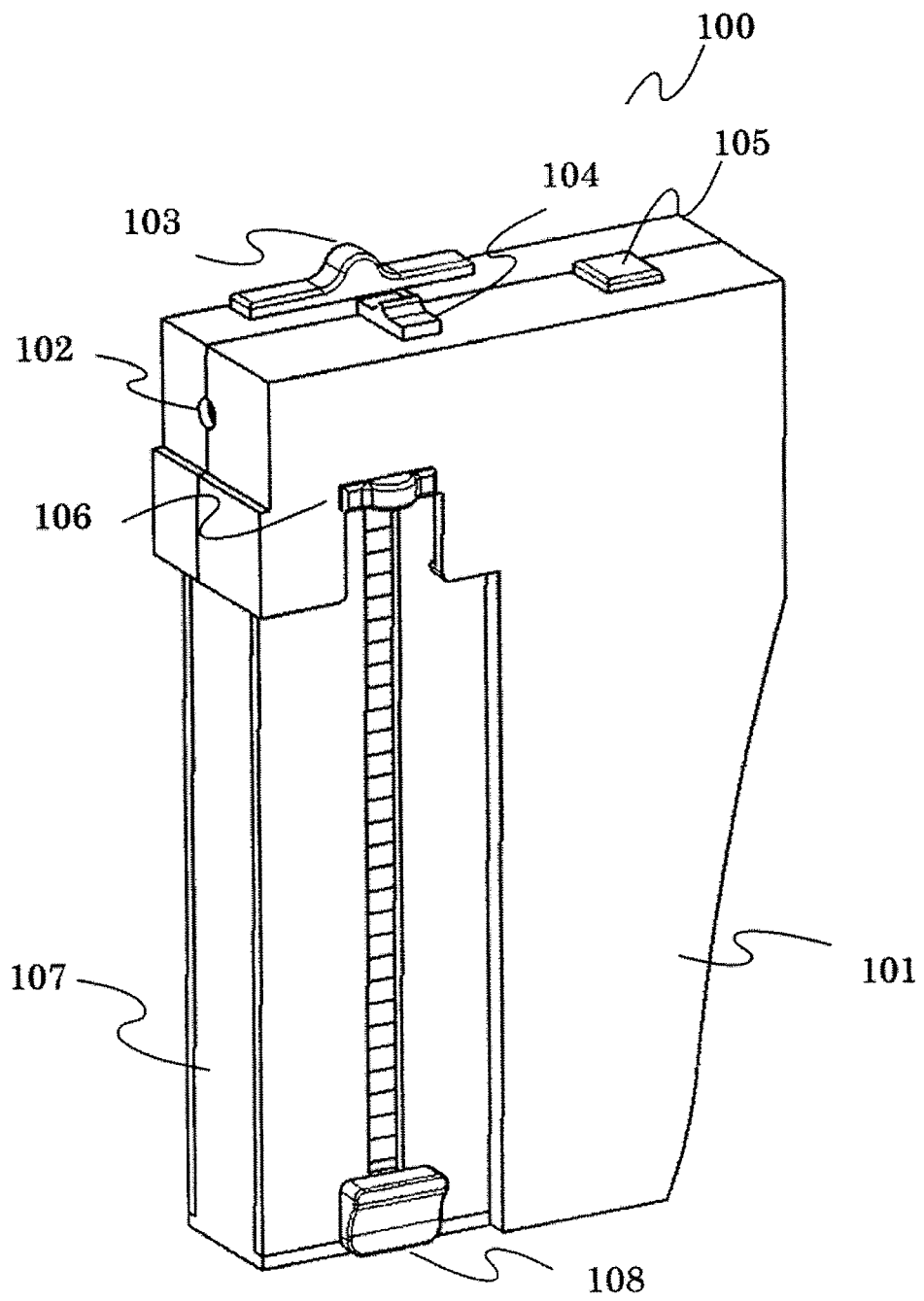
FIG. 2 is an external perspective view of a blood sampling puncturing device according to Embodiment 1 of the present invention.

FIG. 2 is an external perspective view of a blood sampling puncturing device according to Embodiment 1 of the present invention.

As shown in FIG. 2, blood sampling puncturing device 100 includes puncturing device body 101 made of resin and having an approximately rectangular solid shape.

Puncturing opening 102 allowing a lancet needle for puncturing to pass through is open in a side surface of puncturing device body 101.

Puncturing device body 101 includes charging lever 103 to charge puncturing lancets to perform puncturing, depth adjusting lever 104 to adjust the puncturing depth, puncturing button 105 to eject the charged puncturing lancet and stopper 106 that limits operations of the magazine in order to prevent ejection even if the button is pressed erroneously. In addition, magazine 107 is mounted in puncturing device body 101.

Needle feeding lever 108 is provided in magazine 107 and has a function to set one-by-one lancets stored in magazine 107. In addition, needle feeding lever 108 cannot move while stopper 106 is enabled.

Figure 3A:
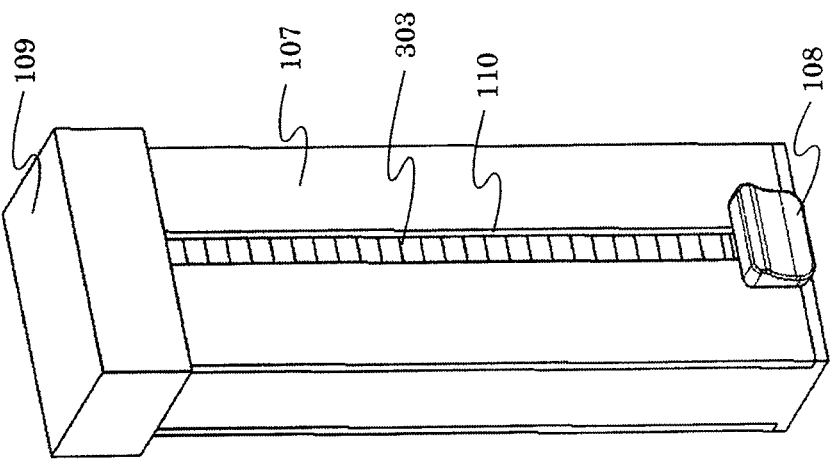
FIG. 3A is an exploded perspective view of the puncturing device body of the blood sampling puncturing device according to Embodiment 1.
Figure 3B:
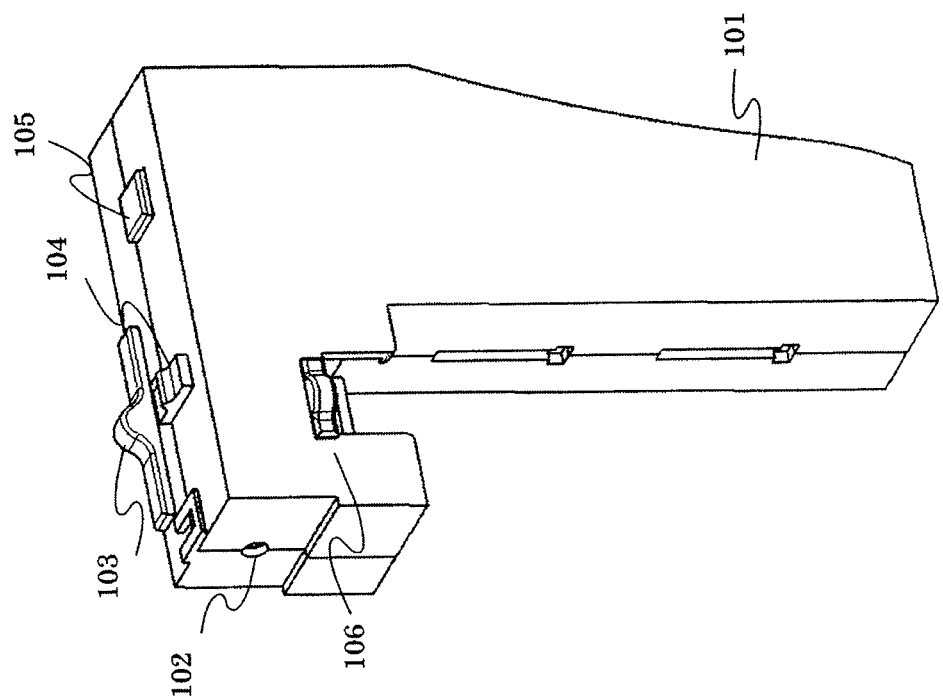
FIG. 3B is an exploded perspective view of a magazine in the blood sampling puncturing device according to Embodiment 1.

FIGS. 3A and 3B are perspective views showing blood sampling puncturing device 100 separated into puncturing device body 101 and magazine 107. FIG. 3A is an external perspective view of puncturing device body 101 and FIG. 3B is an external perspective view of magazine 107.

As shown in FIG. 3B, magazine 107 has magazine cap 109 that protects magazine 107 and check window 110 that allows viewing of the remaining number of the lancets stored in magazine 107.

Magazine cap 109 is used, for example, when the magazine is separately carried, in order not to touch needle part.

A plurality of lancets 303 are accommodated in magazine 107. Magazine 107 has inside a dedicated storing section described later, which stores used lancets separately.

Figure 4:
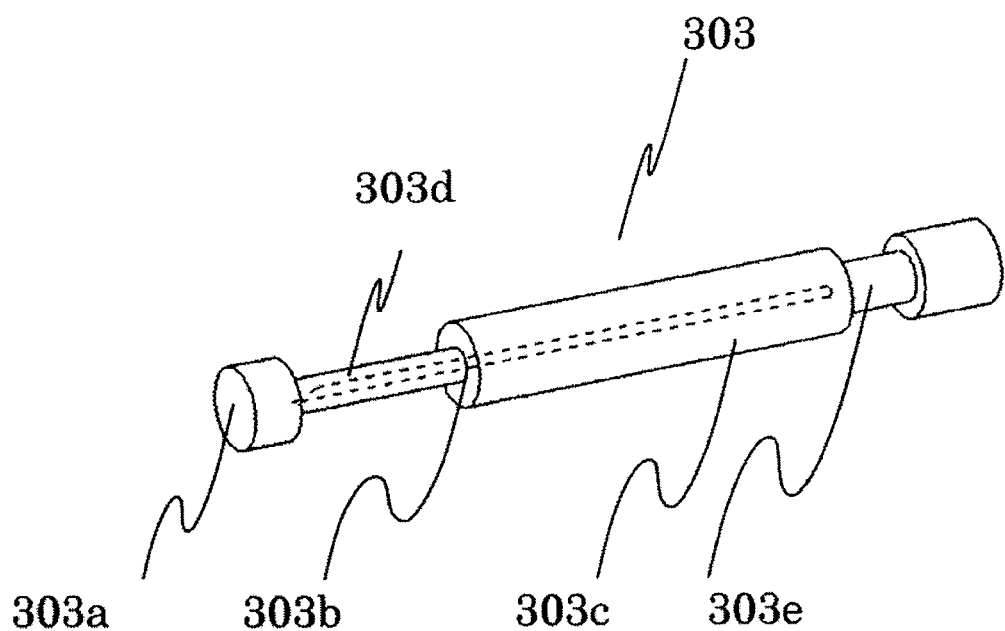
FIG. 4 is a perspective view of a lancet used in the blood sampling puncturing device according to Embodiment 1.

FIG. 4 is a perspective view of lancet 303 used in blood sampling puncturing device 100.

As shown in FIG. 4, lancet 303 includes lancet body 303c having puncturing needle 303d and protective cap 303a that protects puncturing needle 303d. Lancet body 303c and protective cap 303a are made of a resin material and formed integrally by, for example, polyethylene resin. There is separating part (tear-off part) 303b between lancet body 303c and protective cap 303a.

Figure 5:
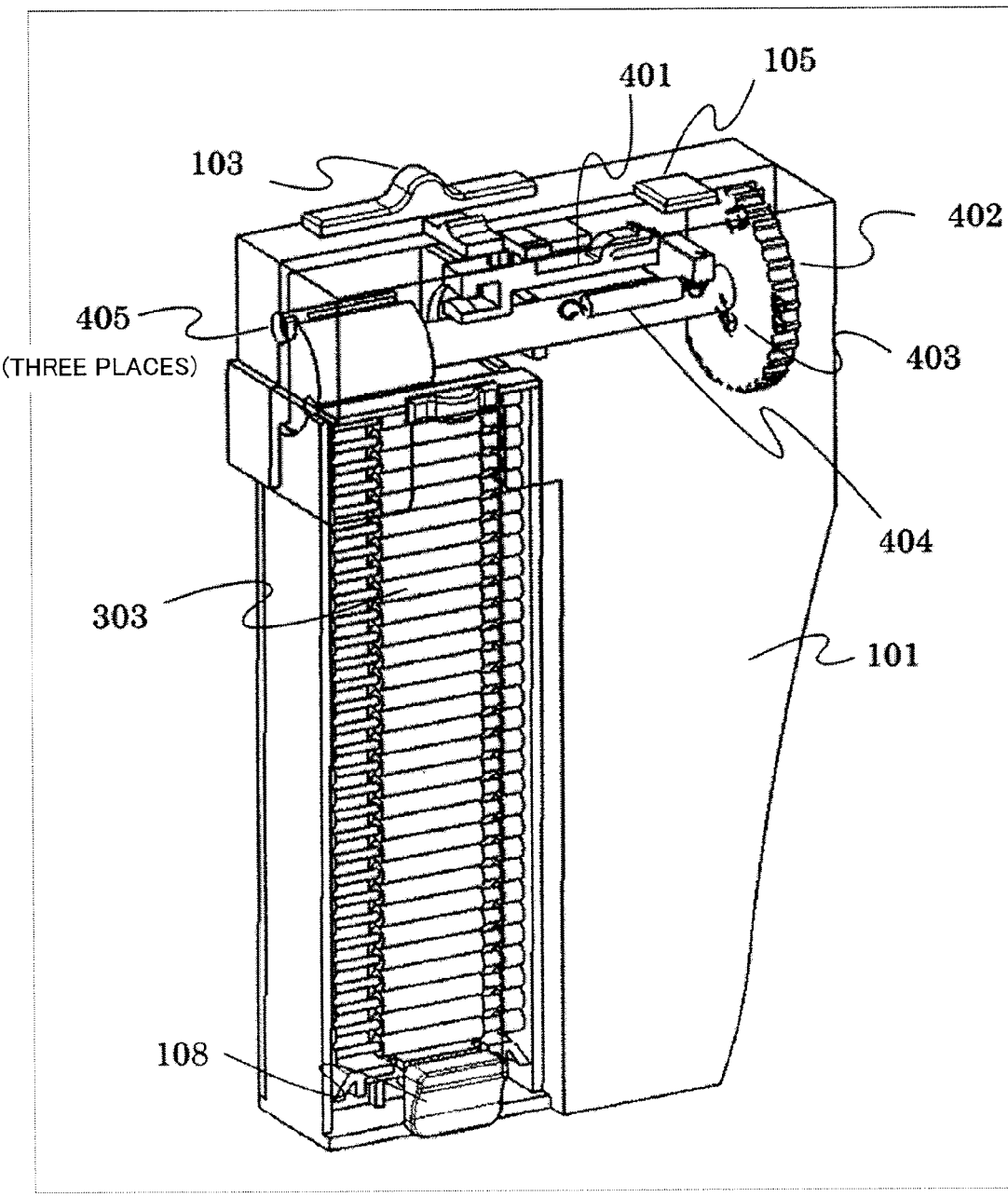
FIG. 5 is a perspective view transparently showing primary parts in the blood sampling puncturing device according to Embodiment 1.

FIG. 5 is a perspective view transparently showing primary parts in blood sampling puncturing device 100. FIG. 5 is a transparent perspective view of puncturing device body 101 (including magazine 107) shown in FIG. 2 and shows a state in which a plurality of lancets 303 are stored in magazine 107.

As shown in FIG. 5, plunger 401, rotation rotor 402, rotation limiting section 403, spring 404 and lancet holding holes 405 are provided inside puncturing device body 101.

Plunger 401 holds lancet 303 and moves the lancet when the lancet is charged for puncturing and performs puncturing.

Rotation rotor 402 has a function to separately supply lancets 303 in magazine 107 one-by-one lancets 303 to lancet holding holes 405 provided in front of rotation rotor 402.

Rotation limiting section 403 limits the rotating direction of rotation rotor 402 to prevent rotation rotor 402 from rotating in the opposite direction.

Spring 404 biases in the puncturing direction in actual puncturing. Spring 404 is contracted by charging lever 103 and accumulates a biasing force for puncturing. Spring 404 is released by puncturing button 105 to eject lancet 303 toward skin.

Figure 6:
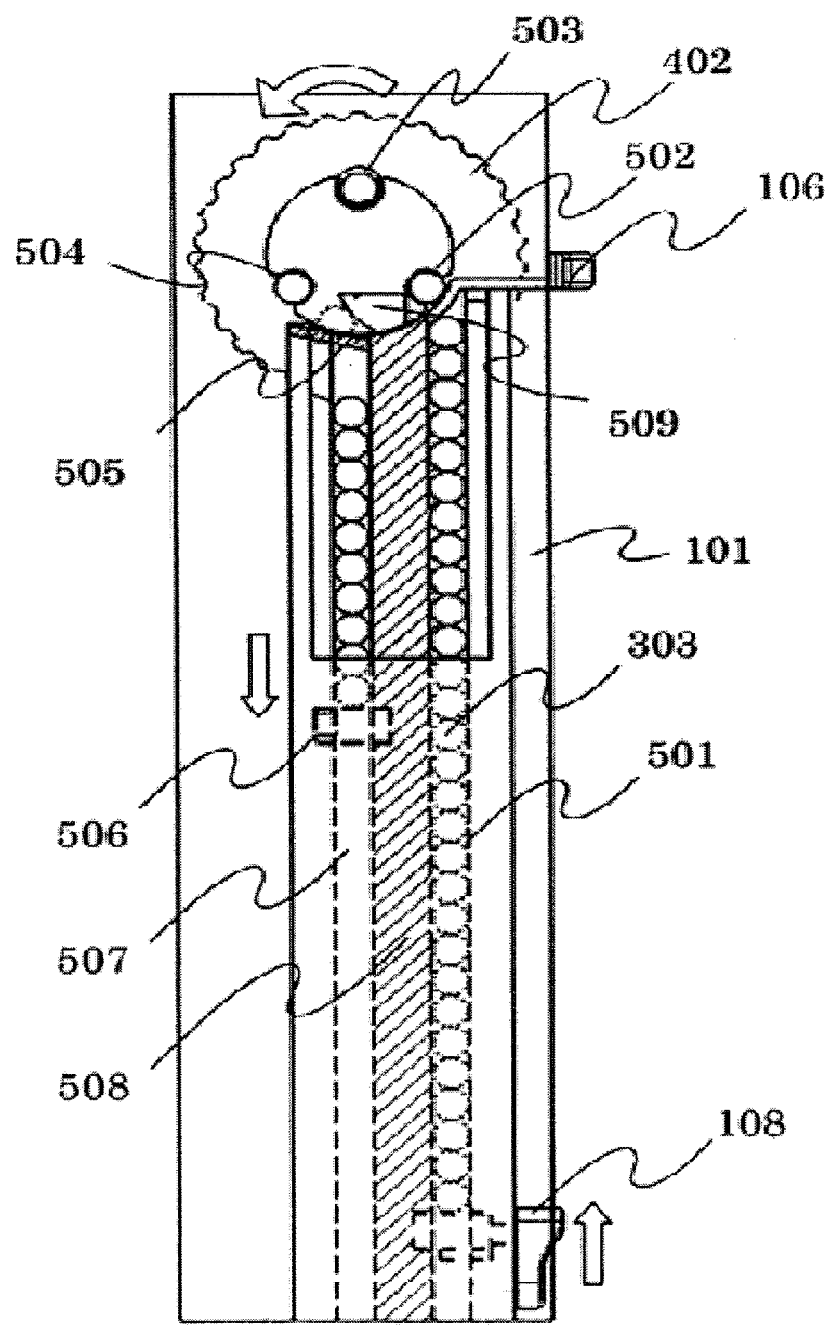
FIG. 6 is a front cross sectional view of the puncturing device body of the blood sampling puncturing device and the magazine according to Embodiment 1.

FIG. 6 is a front cross sectional view of puncturing device body 101 and magazine 107.

As shown in FIG. 6, puncturing device body 101 includes first storing section 501 that stores lancets 303 before use, storing inlet 505, discard needle feeding lever 506, second storing section 507 that stores used lancets to be discarded, storing section partition plate 508 and discarding rib 509.

Numbers 502, 503 and 504 in FIG. 6 indicate the stocking position, the puncturing position and the discarding position, respectively.

Stocking position 502 is a position to separate the top lancet 303 in first storing section 501 and move it to lancet holding hole 405. Puncturing position 503 is a position to charge a lancet and perform a puncturing operation. Discarding position 504 indicates a position to discard the lancet after puncturing with the lancet.

Here, lancet holding holes 405 are provided in three places and arranged at even intervals and equiangularly about the axis of the rotation rotor.

Storing inlet 505 is an opening part to take used lancets to be discarded into second storing section 507.

Discard needle feeding lever 506 indicates the position of the bottom used lancet in the second storing section 507 and moves every time a used lancet is collected.

Storing section partition plate 508 physically separates between first storing section 501 and second storing section 507.

Discarding rib 509 has a function to limit to collect used lancets into storing inlet 505.

Now, operations of the blood sampling puncturing device configured as described above will be explained.

Operation of Lancet 303 at the Time of Puncturing

As shown in FIG. 4, at the time of puncturing, protective cap 303a is torn from separating part 303b to expose the inner puncturing needle 303d. Plunger-held section 303e is held by plunger 401 (see FIG. 5) provided inside puncturing device body 101, and therefore, lancet 303 is held.

Operations of Blood Sampling Puncturing Device 100

First, operations of rotation rotor 402 will be explained.

FIGS. 7A to 7D are cross sectional views of primary parts explaining operations of blood sampling puncturing device 100 and each show a state in which lancet 303 moves resulting from the operation of rotation rotor 402.

Figure 7A:
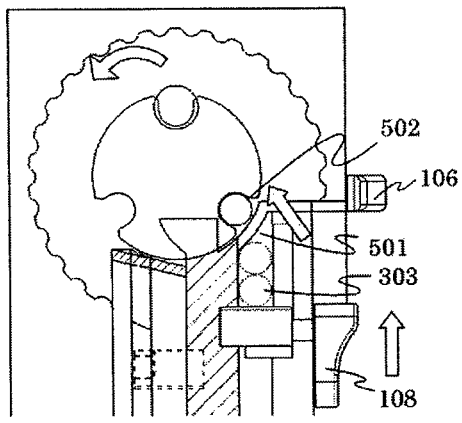
FIG. 7A is a cross sectional view of primary parts explaining operations of the blood sampling puncturing device according to Embodiment 1.

As shown in FIG. 7A, lancets 303 before use stored in first storing section 501 are conveyed to stocking position 502 by pressing upward needle feeding lever 108 after stopper 106 is released. In a state in which stopper 106 is not released, first storing section 501 and puncturing device body 101 are separated from one another.

Figure 7B:
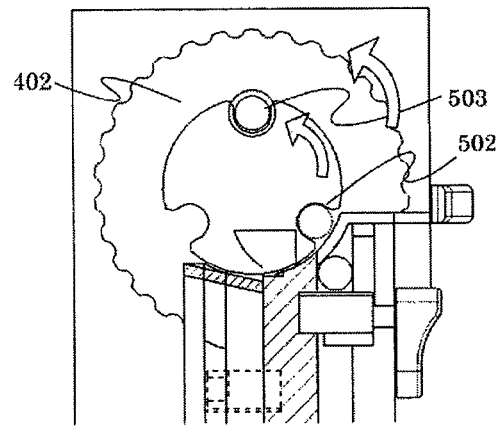
FIG. 7B is a cross sectional view of primary parts explaining operations of the blood sampling puncturing device according to Embodiment 1.

As shown in FIG. 7B, lancet 303 fed to stocking position 502 is conveyed from stocking position 502 to puncturing position 503 by rotation of rotation rotor 402 in the direction of the arrow.

Figure 7C:
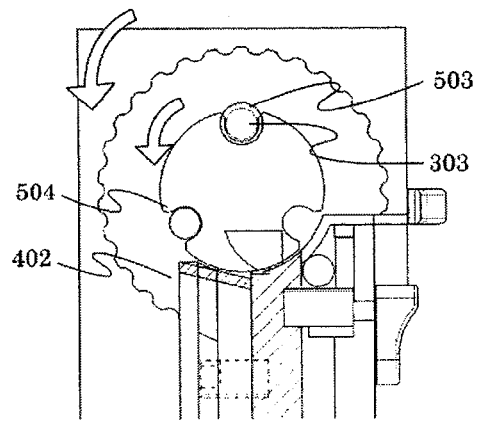
FIG. 7C is a cross sectional view of primary parts explaining operations of the blood sampling puncturing device according to Embodiment 1.

As shown in FIG. 7C, lancet 303 fed to puncturing position 503 is conveyed from puncturing position 503 to discarding position 504 by rotation rotor 402.

Figure 7D:
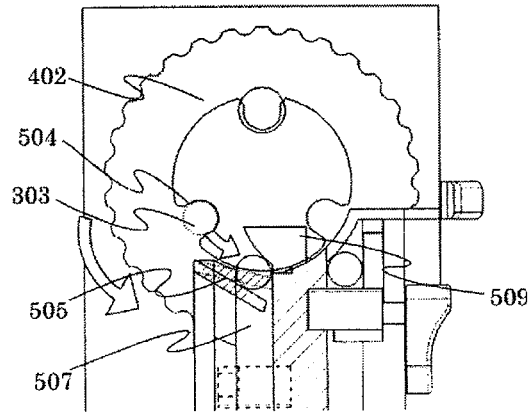
FIG. 7D is a cross sectional view of primary parts explaining operations of the blood sampling puncturing device according to Embodiment 1.

As shown in FIG. 7D, lancet 303 fed to discarding position 504 is conveyed from discarding position 504 to discarding vent 505 by rotation rotor 402, and finally, stored in second storing section 507 from the partition plate of discarding vent 505 being open due to an action of discarding rib 509. Used lancets 303 are isolated in second storing section 507 by the partition plate of discarding vent 505.

Lancet 303 is conveyed to stocking position 502, puncturing position 503 and discarding position 504 in sequence by rotation rotor 402. Rotation limiting section 403 (see FIG. 5) prevents rotation rotor 402 from rotating in the opposite direction, so that lancets after use do not return to first storing section 501 but are stored certainly in second storing section 507. Then, one lancet 303 is taken out from first storing section 501 in magazine 107, passes through the stocking position, performs a puncturing operation in the puncturing position, passes through discarding position 504 and is stored in second storing section 507. After this one cycle is finished, a new lancet is taken out and the next puncturing operation is performed.

By this means, lancets before use and lancets after use are separately stored, so that it is possible to ensure sanitation and safety against infection, which are problems with conventional magazine type puncturing devices.

Next, operations of the puncturing driving section will be explained.

Figure 8:
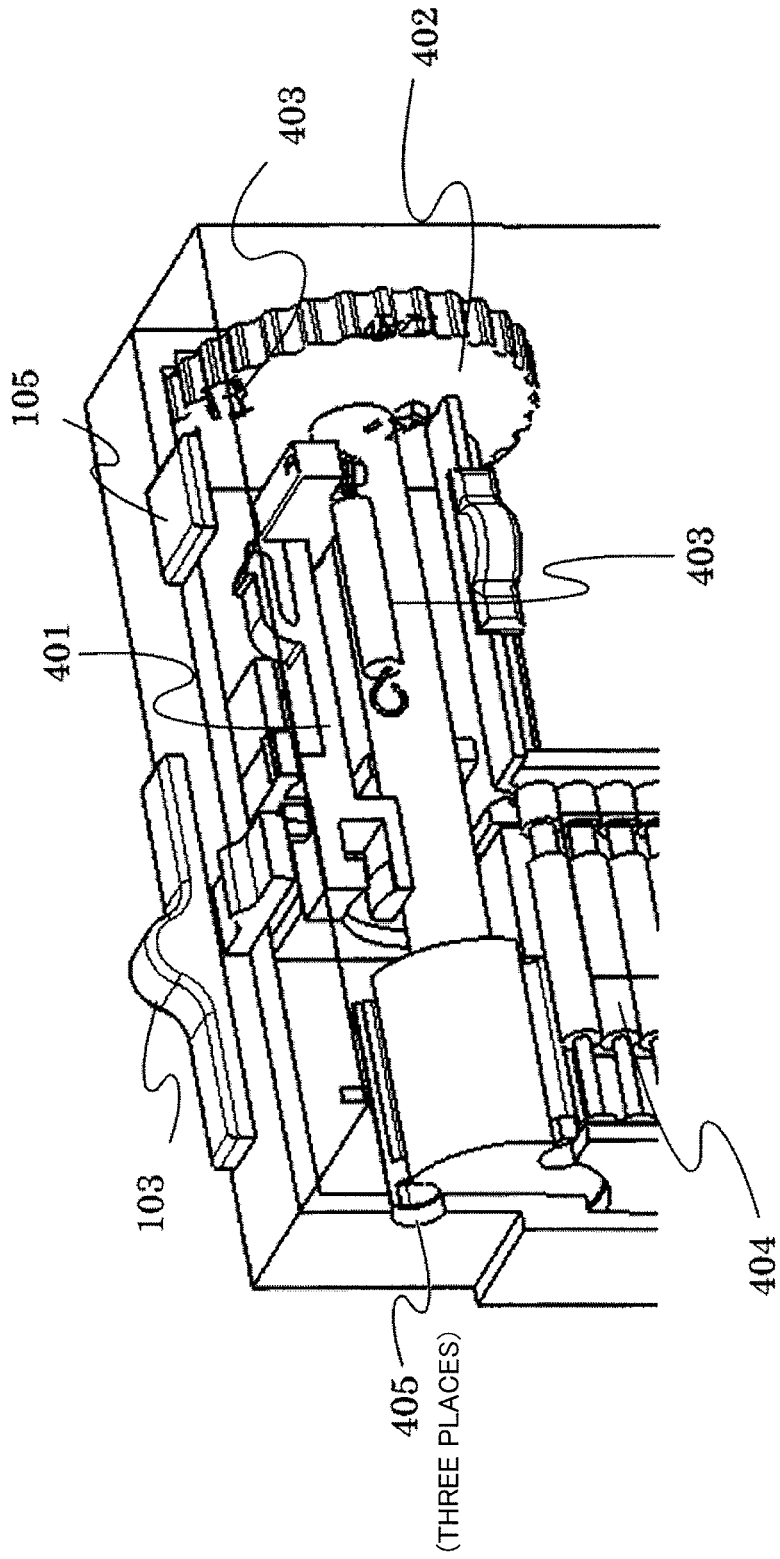
FIG. 8 is a transparent perspective view of a puncturing driving section and its neighboring primary parts in the blood sampling puncturing device according to Embodiment 1.

FIG. 8 is a transparent perspective view of a puncturing driving section and its neighboring primary parts in blood sampling puncturing device 100. FIGS. 9A to 9F are perspective views of primary parts explaining operations of the blood sampling puncturing device and each show a state of the puncturing driving section in operation.

Figure 9A:
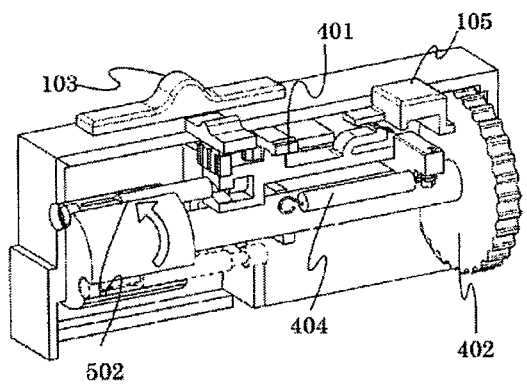
FIG. 9A is a cross sectional view of primary parts explaining operations of the blood sampling puncturing device according to Embodiment 1.

As shown in FIG. 8 and FIG. 9A, lancet 303 is conveyed to puncturing position 502 by rotating rotation rotor 402 and held by plunger 401.

Figure 9B:
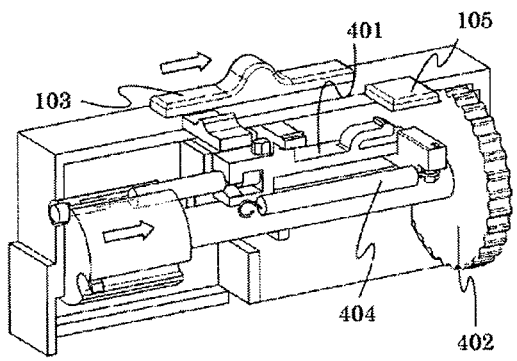
FIG. 9B is a cross sectional view of primary parts explaining operations of the blood sampling puncturing device according to Embodiment 1.

FIG. 9B shows a state in which charging by charging lever 103 is under way.

Figure 9C:
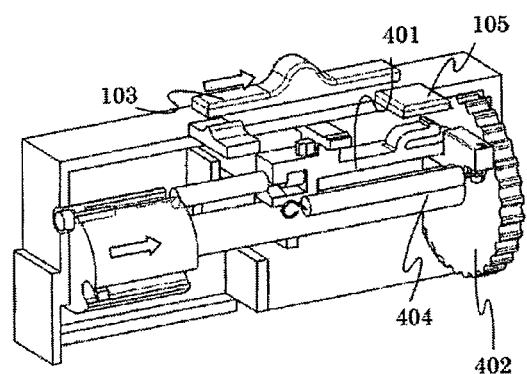
FIG. 9C is a cross sectional view of primary parts explaining operations of the blood sampling puncturing device according to Embodiment 1.

FIG. 9C shows the time of competing charging. Lancet 303 is set in the charging position by moving charging lever 103 in the opposite direction to the puncturing direction. At the same time lancet 303 is charged, protective cap 303a of lancet 303 is separated from separating part 303b of lancet body 303c by rotation rotor 402 and plunger 401.

Figure 9D:
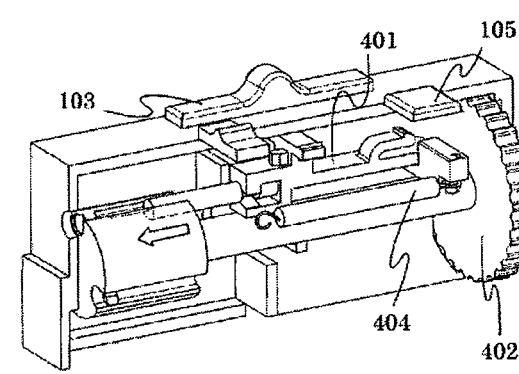
FIG. 9D is a cross sectional view of primary parts explaining operations of the blood sampling puncturing device according to Embodiment 1.

FIG. 9D shows a state in which puncturing button 105 is pressed after charging and a puncturing operation is under way.

Figure 9E:
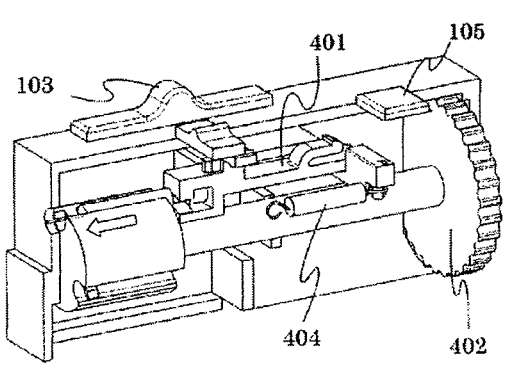
FIG. 9E is a cross sectional view of primary parts explaining operations of the blood sampling puncturing device according to Embodiment 1.

FIG. 9E shows a state in which lancet 303 punctures an object such as skin and so forth by biasing spring 404 in the puncturing direction.

Figure 9F:
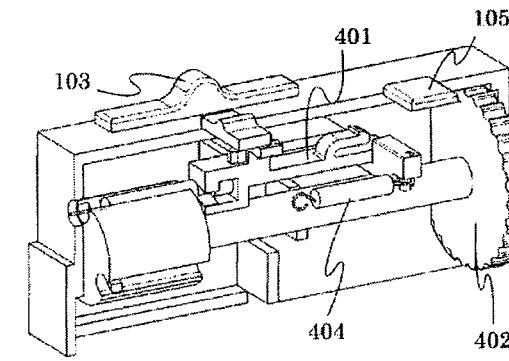
FIG. 9F is a cross sectional view of primary parts explaining operations of the blood sampling puncturing device according to Embodiment 1.

FIG. 9F shows a state in which lancet 303 returns after puncturing.

As described above in detail, according to the present embodiment, blood sampling puncturing device 100 has blood sampling puncturing device body 101 removably incorporating magazine 107 that stores a plurality of lancets to puncture skin. This puncturing device body 101 includes first storing section 501 that store lancets 303 before use and second storing section 507 that stores used lancets 303 to be discarded. Lancets 303 are conveyed one-by-one to stocking position 502, puncturing position 503 and discarding position 504 in sequence by rotating rotation rotor 402. Lancets 303 before use are stored in first storing section 501 and lancet 303 after use are stored in second storing section 507 to separately store in spaces isolated from one another. This configuration allows storage of lancets such that lancets before use and lancets after use are stored separate spaces isolated from one another, so that it is possible to improve sanitation and safety by prevention of inflection.

Embodiment 2

Figure 10:
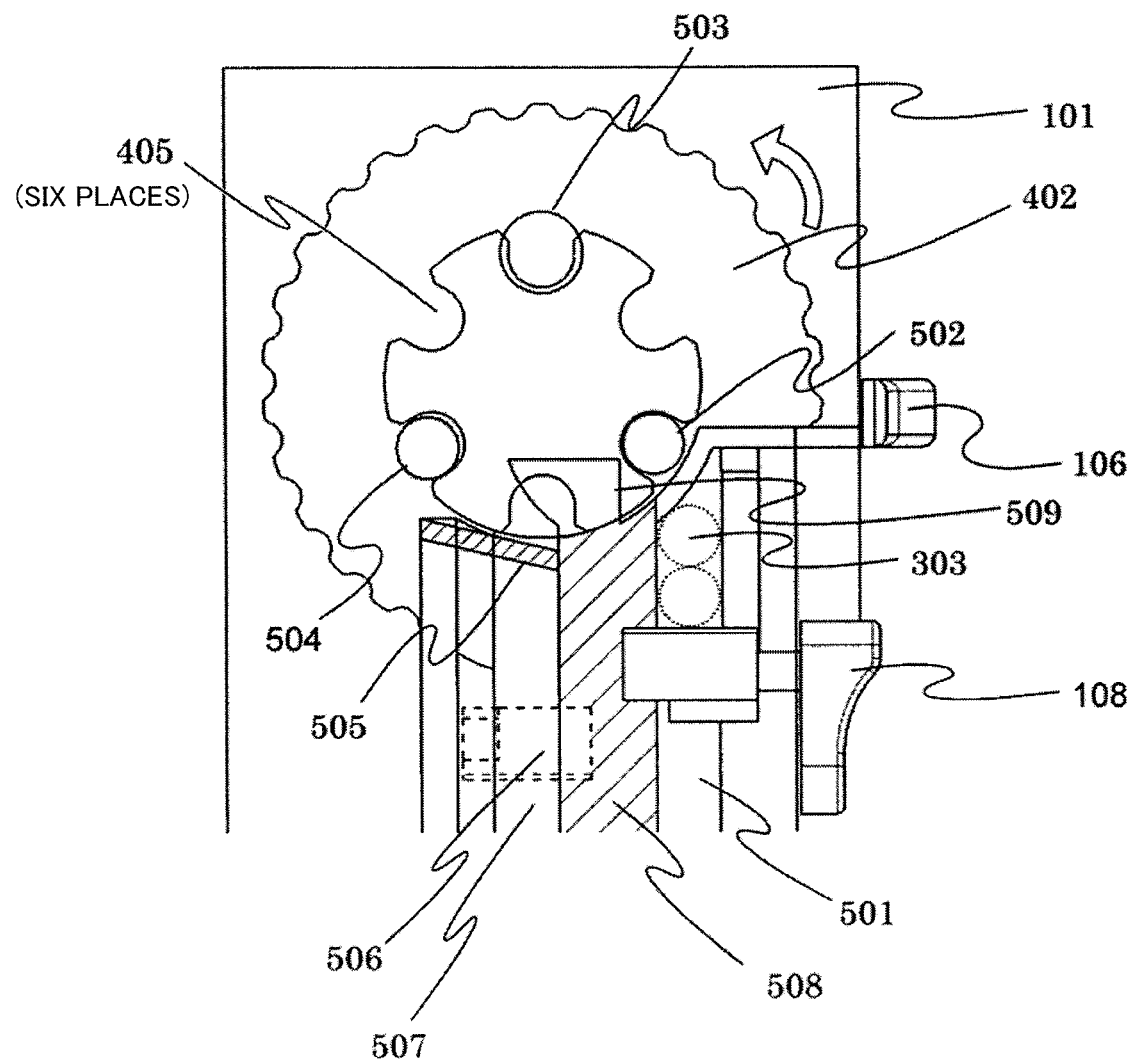
FIG. 10 is a cross sectional view explaining operations of a blood sampling puncturing device according to Embodiment 2 of the present invention.

FIG. 10 is a cross sectional view explaining operations of a blood sampling puncturing device according to Embodiment 2 of the present invention. The same components as in FIGS. 9A to 9F will be assigned the same reference numerals and overlapping descriptions will be omitted.

While the above-described Embodiment 1 has three lancet holding holes 405 in rotation rotor 402, Embodiment 2 has six lancet holding holes 405.

Basic operations of Embodiment 2 are the same as those of Embodiment 1 but the number of lancet holding holes 405 differs from Embodiment 1. Since the number of lancet holding holes 405 is greater, it is possible to reduce the number of rotations of the rotation rotor after a lancet is discarded until the next lancet is held in the stocking position.

In the same way as the above-described Embodiment 1, a lancet 303 is conveyed to stocking position 502, puncturing position 503 and discarding position 504 in sequence by rotating rotation rotor 402 in the direction of the arrow.

Here, lancet holding holes 405 are provided in six places and arranged at even intervals and equiangularly about the axis of the rotation rotor.

Embodiment 3

Figure 11:
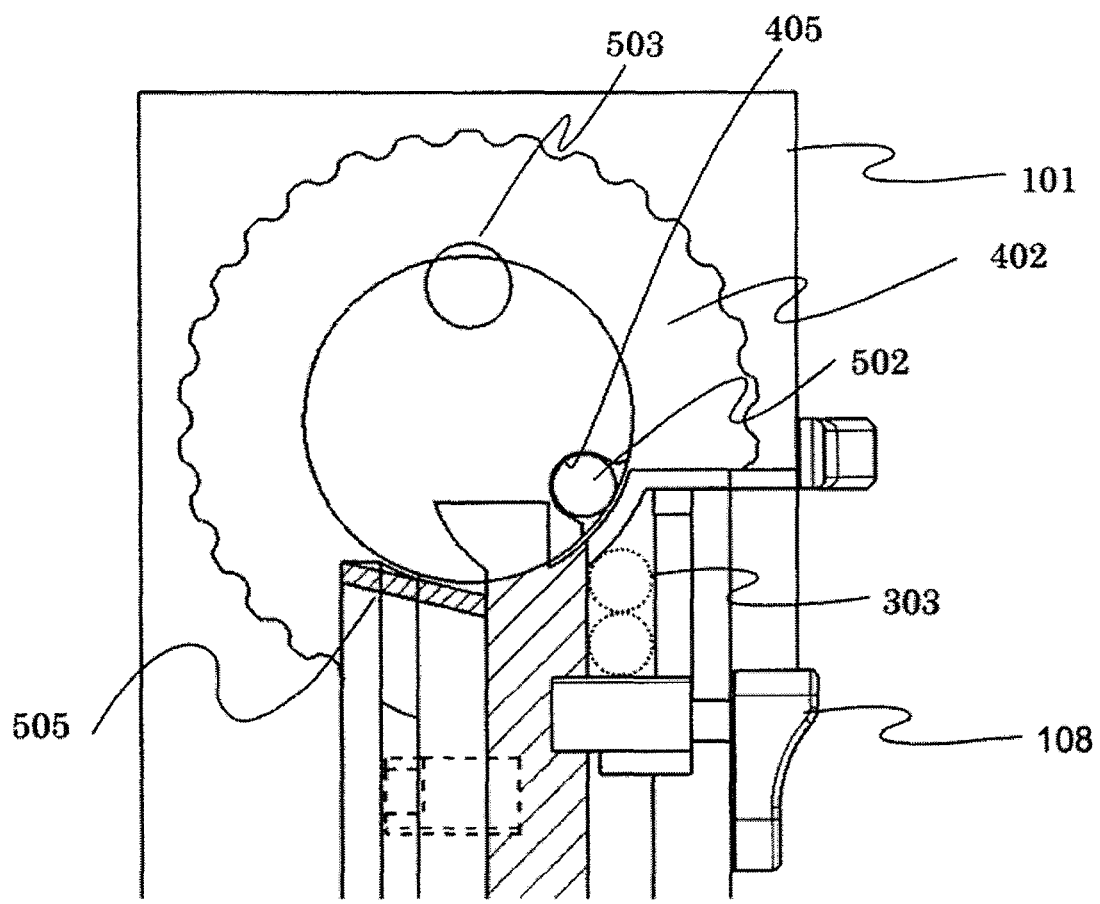
FIG. 11 is a cross sectional view explaining operations of a blood sampling puncturing device according to Embodiment 3 of the present invention.

FIG. 11 is a cross sectional view explaining operations of a blood sampling puncturing device according to Embodiment 3 of the present invention. The same components as in FIGS. 9A to 9F will be assigned the same reference numerals and overlapping descriptions will be omitted.

While the above-described Embodiment 1 has three lancet holding holes 405 in rotation rotor 402, Embodiment 3 has one lancet holding hole 405.

In the same way as the above-described Embodiment 1, Embodiment 3 allows one cycle of a puncturing operation from stocking position 502 through puncturing position 503 to discarding position 504 by rotating rotation rotor 402 once. Lancet 303 is conveyed from the stocking position through the puncturing position to the discarding position by rotating rotation rotor 402 in the direction of the arrow.

According to Embodiment 3, there is only one lancet holding hole 405, so that it is possible to prevent another lancet from being set in the rotation rotor by an incorrect operation.

The above description is illustration of preferred embodiments of the present invention and the scope of the invention is not limited to this.

Although the name "blood sampling puncturing device" is used in each of the above-described embodiments for ease of explanation, "puncturing device", "puncturing lancet" and so forth are possible.

The type, the number, the connection method and so forth of each of parts constituting the above-described blood sampling puncturing device, such as a rotation rotor and a conveying mechanism, are not limited.

The disclosure of Japanese Patent Application No. 2008-069043, filed on Mar. 18, 2008, including the specification, drawings and abstract, is incorporated herein by reference in its entirety.

INDUSTRIAL APPLICABILITY

The blood sampling puncturing device and the magazine according to the present invention are applicable to a blood sampling puncturing device and so forth having a magazine that stores separately lancets before use and lancets after use as measures to provide sanitation in the magazine and assure safety by prevention of infection.

What is claimed is:

1. A blood sampling puncturing device comprising:
a magazine storing a plurality of lancets each having a needle to puncture skin; and
a rotation rotor that is located outside of the magazine and configured to hold at least one lancet of the plurality of lancets, the magazine being removably mounted in the blood sampling puncturing device, wherein
the magazine has a first storing section that is configured to store lancets before use therein, a second storing section that is configured to store lancets after use therein, and a partition plate that closes the second storing section, the first storing section defining a space therein and the second storing section defining a space therein, the space of the first storing section and the space of the second storing section being physically separated from one another by the partition plate, and the partition plate being configured to open the second storing section upon storing the at least one lancet in the second storing section, and
the rotation rotor has at least one lancet holding hole provided at a circumferential surface of the rotation rotor, the lancet holding hole being configured to remove at least one lancet of the plurality of lancets stored in the space of the first storing section in the magazine, to an outside of the magazine, by rotation, to hold the removed lancet in the lancet holding hole and to further rotate the lancet held in the lancet holding hole into a puncturing position for a puncturing operation, and when the puncturing operation has been performed the rotation rotor is configured to further rotate the lancet held in the lancet holding hole to the second storing section in the magazine to release the lancet into the space of the second storing section.

2. The blood sampling puncturing device according to claim 1, further comprising one or more holding positions to hold the at least one lancet removed from the first storing section of the magazine.

3. The blood sampling puncturing device according to claim 2, wherein the holding positions include a stocking position to prepare and to hold the at least one lancet removed from the first storing section prior to the puncturing operation, the puncturing position for the puncturing operation, and a discarding position to hold the at least one lancet in the second storing section after the puncturing operation is performed.

4. The blood sampling puncturing device according to claim 3, wherein the rotation rotor is configured to convey the at least one lancet to the stocking position, the puncturing position and the discarding position in sequence.

5. The blood sampling puncturing device according to claim 4, further comprising:
a needle feeding lever configured to separate the at least one lancet from the plurality of lancets stored in the first storing section and to hold the at least one lancet in the stocking position; and
a stopper to lock the needle feeding lever.

6. The blood sampling puncturing device according to claim 4, further comprising a discarding rib that that is configured to remove the at least one lancet at the discarding position from the rotation rotor so as to store the at least one lancet in the second storing section during a rotation of the rotation rotor.

7. The blood sampling puncturing device according to claim 1, wherein the rotation rotor has a rotation limiting section that limits rotation to only one direction.

8. The blood sampling puncturing device according to claim 1, wherein the rotation rotor is rotatable in one of a clockwise direction and a counterclockwise direction about a rotation axis.

9. The blood sampling puncturing device according to claim 1, wherein the lancet holding hole is arranged at even intervals on the rotation rotor.

10. The blood sampling puncturing device according to claim 1, further comprising a puncturing section that performs the puncturing operation with the at least one lancet in the puncturing position.

11. The blood sampling puncturing device according to claim 10, wherein the puncturing section includes:
a plunger;
a spring that biases the plunger in a puncturing direction;
a charging lever that sets the at least one lancet in an ejecting position; and
a puncturing button to eject the at least one lancet.

12. The blood sampling puncturing device according to claim 11, wherein when the rotation rotor conveys the at least one lancet to the puncturing position, the plunger holds the at least one lancet.

13. The blood sampling puncturing device according to claim 12, wherein:
the at least one lancet is composed of a needle and a protective cap that protects the needle; and
when the plunger holds the at least one lancet, the spring is charged by a movement of the charging lever, and the protective cap of the lancet is separated by a cooperation of the rotation rotor and the plunger.

14. The blood sampling puncturing device according to claim 1, the magazine further comprising a check window that indicates a remaining number of the plurality of lancets in the first storing section before use.

15. The blood sampling puncturing device according to claim 1, wherein the plurality of lancets before use are stored in the first storing section such that the lancets are aligned parallel with each other.

* * * * *